United States Patent
Aoki et al.

(10) Patent No.: US 7,431,700 B2
(45) Date of Patent: Oct. 7, 2008

(54) BODY MOVEMENT AND RESPIRATION MONITOR

(75) Inventors: Hirooki Aoki, Tokyo (JP); Masato Nakajima, Tokyo (JP); Yasuhiro Takemura, Tokyo (JP); Kazuhiro Mimura, Tokyo (JP)

(73) Assignees: KEIO University, Tokyo (JP); Sumitomo Osaka Cement Co., Ltd., Tokyo (JP)

( * ) Notice: Subject to any disclaimer, the term of this patent is extended or adjusted under 35 U.S.C. 154(b) by 676 days.

(21) Appl. No.: 10/432,632

(22) PCT Filed: Dec. 6, 2001

(86) PCT No.: PCT/JP01/10685

§ 371 (c)(1),
(2), (4) Date: Nov. 20, 2003

(87) PCT Pub. No.: WO02/45585

PCT Pub. Date: Jun. 13, 2002

(65) Prior Publication Data

US 2004/0082874 A1    Apr. 29, 2004

(30) Foreign Application Priority Data

Dec. 7, 2000 (JP) ............................. 2000-372820

(51) Int. Cl.
*A61B 5/08* (2006.01)
*A61B 5/103* (2006.01)
*A61B 5/117* (2006.01)

(52) U.S. Cl. .................. 600/534; 600/595; 600/529

(58) Field of Classification Search ................ 600/300, 600/301, 529–543, 595

See application file for complete search history.

(56) References Cited

U.S. PATENT DOCUMENTS 4,738,266 A * 4/1988 Thatcher .................... 600/473
4,928,703 A * 5/1990 Wong ........................ 600/532

(Continued)

FOREIGN PATENT DOCUMENTS

DE    31 09 026    9/1982

(Continued)

OTHER PUBLICATIONS

The Supplementary European Search Report for corresponding European patent application No. 01 99 9317, dated Apr. 5, 2006. (Citing References AA-AB and AF-AJ).

*Primary Examiner*—Charles A. Marmor, II
*Assistant Examiner*—Navin Natnithithadha
(74) *Attorney, Agent, or Firm*—Edwards Angell Palmer & Dodge LLP

(57) ABSTRACT

A monitor which can detect respiration of a sleeping person without being affected by the attitude of the sleeping person or the indoor illumination light and can easily evaluate detected respiration quantitatively through image measurement. The monitor comprises means (1) for projecting a specified illumination pattern, means (5) for picking up the image of projected light continuously, means (7) for calculating inter-frame moving amount of the illumination pattern from the image of two frames acquired by the image pickup means at different times, means (8) for generating a moving amount waveform data comprising inter-frame moving amounts arranged in time series, and means (9) for detecting the movement of an object from the moving amount waveform data.

22 Claims, 13 Drawing Sheets

U.S. PATENT DOCUMENTS

| | | | |
|---|---|---|---|
| 5,107,845 A | | 4/1992 | Guern et al. |
| 5,309,921 A | * | 5/1994 | Kisner et al. ............... 600/532 |
| 5,482,042 A | * | 1/1996 | Fujita ........................ 600/428 |
| 5,800,360 A | * | 9/1998 | Kisner et al. ............... 600/532 |
| 6,062,216 A | | 5/2000 | Corn |
| 6,492,634 B2 | * | 12/2002 | Marchitto et al. .......... 250/221 |
| 7,035,432 B2 | * | 4/2006 | Szuba ........................ 382/103 |

FOREIGN PATENT DOCUMENTS

| | | |
|---|---|---|
| FR | 1570640 | 6/1969 |
| JP | 5-161613 | 6/1983 |
| JP | 61-25542 | 2/1986 |
| JP | 7-327939 | 12/1995 |
| JP | 11-28195 | 2/1999 |
| JP | 11-86002 | 3/1999 |
| JP | 11-225997 | 8/1999 |
| JP | 2000-83027 | 3/2000 |
| JP | 2000-107154 | 4/2000 |
| WO | 90/09560 | 8/1990 |
| WO | 97/26824 | 7/1997 |
| WO | 01/82785 | 11/2001 |

\* cited by examiner

FIG.2
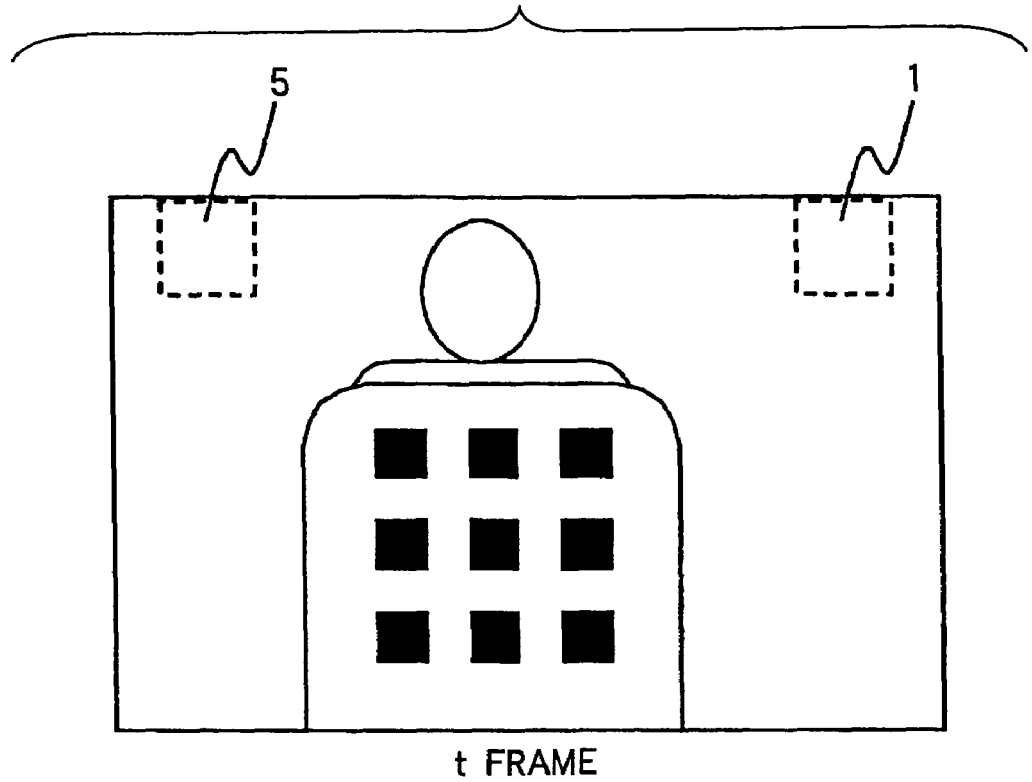
t FRAME
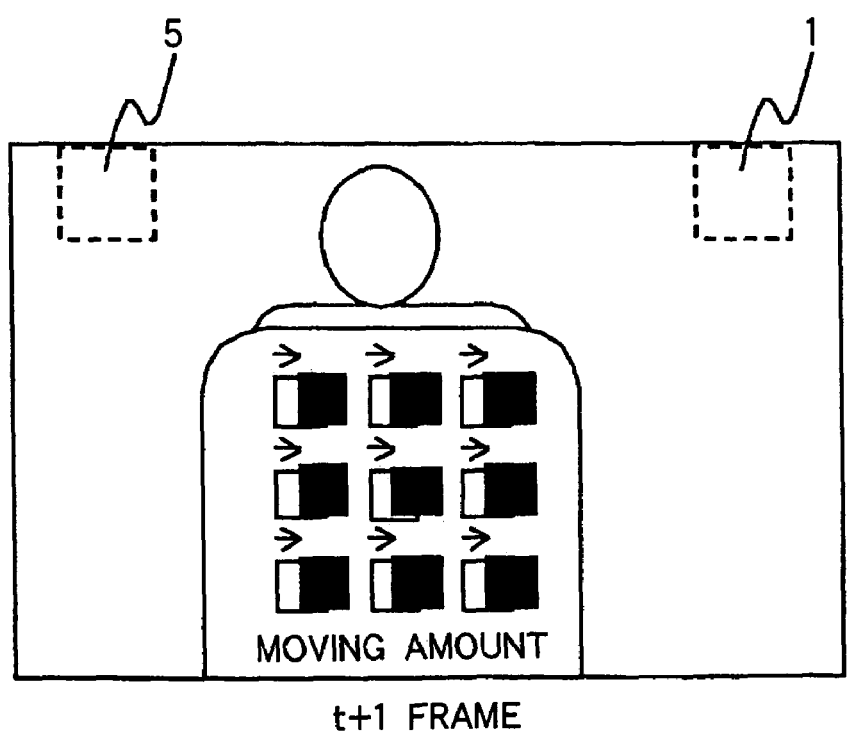
t+1 FRAME

SINGLE BREATH TIME

FIG.8
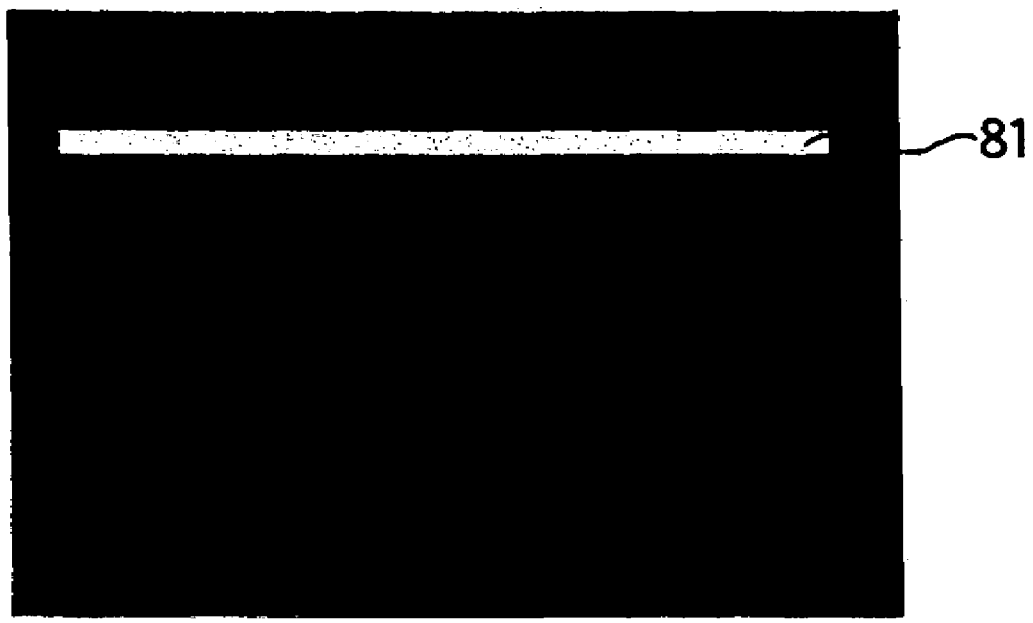

BODY MOVEMENT AND RESPIRATION MONITOR

The Priority document PCT/JP01/10685 filed on Dec. 6, 2001 is herein incorporated in its entirety into this specification.

TECHNICAL FIELD

The invention of this application relates to a monitor. More particularly, the present invention relates to a monitor capable of monitoring the body movement etc., of a sleeping person in a noncontact manner with image measurement.

BACKGROUND ART

With the advent of an aging welfare society, the importance of home health monitoring for disease prevention and self care is expected to continue to grow, and various bioinstrumentation methods have been proposed. An aged but healthy normal person who can live an ordinary life can be mentioned as an example of a person to be the subject of such home health monitoring. However, under the present circumstances, such a person lacks the motivation to exercise health control and perform a troublesome device operation, because he/she does not need imminent health care. Therefore, a proposal has been made of various bioinstrumentation devices capable of measuring biomedical information under an unconscious condition without any device operation. As measurement methods employed in such bioinstrumentation devices, there are known a method of arranging temperature sensors in a bed or a bottom mattress and, from a temperature distribution, recording body movements at the time of getting into bed, at the time of rising from bed, and during sleep in bed, a method of deriving an electrocardiogram from an electrically conductive sheet and a pillow cover, and a method of measuring respiration and heart beat during sleep by use of a load sensor such as a highly accurate strain gauge or a load cell.

Recently, a proposal has been made to use such bioinstrumentation technology as a security device applied in the safety confirmation of an aged person besides the usage of health monitoring. For example, a leaving-bed sensor has been generally sold for detecting the leaving or falling out of bed of a person during sleep by measuring an electrostatic capacity etc. Additionally, an apnea detector is well known in which an apnea state, caused by an apnea syndrome by which breathing ceases during sleep, is detected by measuring respiration with a pressure-sensitive sensor, and a third party can be informed of the state (e.g., Japanese publication of unexamined patent application No. (hereinafter referred to as JP-A-) 2000-107154).

As a matter of course, respiration provides a very useful clue for immediately knowing the health condition of a person. Respiration measurement performed during sleep is expected to be useful not only in detecting an apnea syndrome but also in discovering a spasmodic incident caused by a sudden attack during sleep. As mentioned above, a typical respiration detecting method during sleep is a method of detecting respiration based on time base measured values of a lead sensor or a pressure-sensitive sensor. Additionally, a method of using a vibration sensor, a radio-wave sensor, or air-pressure detection is publicly known (e.g., JP-A-H7-327939, JP-A-H11-28195, and JP-A-2000-83927). In these methods, since a measured signal is weak, a high-performance signal amplifier or some kind of signal processing is required to acquire and detect a stable signal, and, as a system, it becomes expensive and large in scale.

On the other hand, some proposals have been also made of a method of acquiring an image of a sleeping person by use of an image pickup device and detecting respiration based on the acquired image. With recent developments in electronic equipment, a high-performance image pickup device has appeared on the market at an extremely low price, and, since the device has noncontact properties, the method of detecting respiration based on an image has been brought to public attention as a technique having high practical usefulness.

For example, in "Image-processing device and patient-observing device" of JP-A-H11-86002 and "Region-of-interest setting device of respiration monitoring and respiration-monitoring system" of JP-A-H11-225997, the basic features of those inventions is to monitor respiration by examining a difference between images acquired in different time by the image pickup device.

The "image-processing device and patient-observing device" of JP-A-H11-86002 is composed of a TV camera, a respiration monitoring device, and a local-region automatic setting processing device. The local-region automatic setting processing device is composed of an edge detecting section that detects an edge included in a local region image set on an image for which a patient who requires care is photographed by the TV camera, a brightness distribution measuring section that measures the brightness distribution of each local partial region image divided by the edge in the local region image, and a determining section that sets a local region image to extract movement information by analyzing information about a detected edge and information about a measured brightness distribution. The local region image is divided into a plurality of local partial regions that are identical in brightness, and a time differentiation process is applied to each pixel included in each local partial region, and the total amount of the time differentiation is calculated. A time base change of this amount is analyzed, and a periodic appearance is detected as respiration, whereas irregularities in the period and amplitude are detected as great body movements, such as a body twist.

In the "Region-of-interest setting device of respiration monitoring and respiration-monitoring system" of JP-A-H11-225997, a calculation is first performed of the absolute value of a difference between every one frame of a plurality of frame images picked up by a CCD camera over ½ periods of respiration. Thereafter, the difference images are integrated and stored, the positions and sizes of variation regions are then calculated from variation information that has been integrated and stored, and they are set as temporary regions in order from the largest to the smallest region in the variation ones. Thereafter, a judgment is made of whether a concentration-value histogram, that shows the distribution of the number of pixels of each concentration value, exhibits a two-peak characteristic having a height greater than a predetermined value in the temporary regions and whether the area value of the variation regions is greater than a given value. If this condition is satisfied, the temporary region is set as a region of interest (abbreviated as ROI). Further, a time differentiation process is performed in the set ROI, the absolute value of the difference between each pixel is then obtained, and a surface integral is applied. The surface integral is performed in a time series manner, and, like the invention of JP-A-H11-86002, a time base change in this surface integral is analyzed, and a periodic appearance is detected as respiration, whereas irregularities in the period and amplitude are detected as great body movements, such as a body twist.

Further, a method of detecting respiration by an optical flow of movement of a sleeping person is known as an image-using technique other than the aforementioned methods. The optical flow is characterized by detecting the movement of a sleeping person as a velocity vector, and a respiration waveform having a periodic rhythm and a body-movement waveform having a high peak can be obtained from a vector field by employing the fact that most upward vectors are detected in inspiration whereas most downward vectors are detected in expiration.

The respective methods described above are to observe the movement of shadows on a quilt by use of illumination light, and there remains the fundamental problem of being sometimes incapable of detecting the movement of shadows depending on lighting conditions, the posture of a sleeping person, or the design of the quilt. Additionally, since an image pickup device must be set close to the sleeping person in order to photograph the shadow on the quilt, the respiration monitoring according to the aforementioned methods is considered to entail a psychologically overpowered feeling when the person to be monitored goes to bed.

Additionally, it is said that the method based on a time differentiation can evaluate a frequency of the movement of a targeted person, but cannot make a quantitative evaluation of the movement thereof. In contrast, in the optical-flow method, the optical flow enables a quantitative evaluation of the movement of a sleeping person, but, in practice, much computation time is needed to calculate the optical flow, and there remains the problem of requiring expensive processing equipment.

DISCLOSURE OF INVENTION

Therefore, the invention of this application has been made in consideration of the foregoing circumstances, and it is an object of the invention to provide a monitor capable of detecting respiratory movement of a sleeping person without being affected by the posture of the sleeping person or the indoor illumination light and capable of easily evaluating detected respiratory movement quantitatively through image measurement.

The monitor of the present invention comprises lighting pattern projecting means for projecting a specified lighting pattern, image pickup means for picking up light of projected wavelength continuously, moving amount calculating means for calculating an inter-frame moving a mount of the lighting pattern from two frames of images acquired by the image pickup means at different times, moving amount waveform generating means for generating moving amount waveform data comprising inter-frame moving amounts arranged in time series, and waveform detecting means for detecting a movement of an object to be picked up from the moving amount waveform data.

The waveform detecting means is to detect the body movement and respiratory movement of a sleeping person, and the monitor further comprises safety deciding means for deciding the safety of the sleeping person from the body movement and respiratory movement of the sleeping person and signal outputting means for, when the safety deciding means decides that the sleeping person is in a dangerous state, outputting a signal indicating it.

The moving amount calculating means can easily calculate the moving amount of the lighting pattern by calculating the inter-frame moving amount of the lighting pattern in an axial direction connecting the lighting pattern projecting means and the image pickup means.

The waveform detecting means can detect a respiratory pattern and a body movement pattern by detecting a periodic pattern as the respiratory pattern and by detecting a variation having a high peak as the body movement pattern from moving-amount waveform data.

The safety deciding means can decide a dangerous state of a sleeping person by deciding that the sleeping person is in a dangerous state when a period of the respiratory pattern falls into disarray in a short time, when the period of the respiratory pattern suddenly changes, when the respiratory pattern continuously disappears, or when the body movement pattern frequently appears in a short time.

The moving amount calculating means can easily and reliably detect the movement of an object to be photographed by calculating an inter-frame moving amount of the lighting pattern in an axial direction connecting the lighting pattern projecting means and the image pickup means while providing a positive or negative sign in accordance with a moving direction.

The waveform detecting means can reliably detect a respiratory pattern by, from among respiratory patterns, detecting a value having a positive or negative sign corresponding to a movement in a direction from the lighting pattern projecting means to the image pickup means on an image and a value having a positive or negative sign corresponding to a movement in a direction from the image pickup means to the lighting pattern projecting means on the image as an expiratory pattern and as an inspiratory pattern, respectively, or vice versa.

The waveform detecting means can well adapt to processing in a computer by counting zero crosses where signs are reversed between an expiratory pattern and an inspiratory pattern to count respirations.

The waveform detecting means can further exactly calculate a respiration number per unit time or a respiration period by calculating the respiration number per unit time or the respiration period from the counted respirations.

The waveform detecting means can further easily and exactly calculate a respiration number per unit time or a respiration period by conducting a frequency analysis of moving-amount waveform data or sampling data obtained by sampling respiratory patterns, by calculating the most prominent frequency from a resulting frequency spectrum, and by calculating the respiration number per unit time or the respiration period from this frequency.

The waveform detecting means can further calculate the respiration number per unit time or the respiration period through digital signal processing by conducting a frequency analysis with discrete Fourier transform or discrete wavelet transform.

The safety deciding means can reliably decide that a sleeping person is in a dangerous state by deciding whether respiration belongs to normal respiration, Cheyne-Stokes respiration, central hyperventilation, ataxic respiration, or Kussmaul respiration from expiratory patterns and inspiratory patterns and by deciding that the sleeping person is in a dangerous state when the respiration belongs to any one of Cheyne-Stokes respiration, central hyperventilation, ataxic respiration, and Kussmaul respiration.

The moving amount calculating means calculates an inter-frame moving amount in a partial region of the lighting pattern in an axial direction connecting the lighting pattern projecting means and the image pickup means, and determines a region in an image where an inter-frame moving amount in the partial region appears much greater than a predetermined amount or where an inter-frame movement in the partial region appears frequently beyond a predetermined amount as a region where the sleeping person exists, and the safety deciding means can safely and reliably decide that the sleeping person is in a dangerous state by deciding that the sleeping person is in a dangerous state when the region where the sleeping person exists moves in a shorter time than a predetermined time and moves frequently beyond a predetermined amount.

The moving amount calculating means calculates an inter-frame moving amount in a partial region of the lighting pattern in an axial direction connecting the lighting pattern projecting means and the image pickup means, and determines a region in an image where an inter-frame moving amount in the partial region appears much greater than a predetermined amount or where an inter-frame movement in the partial region appears more frequently than a predetermined frequency as a region where the sleeping person exists, and the safety deciding means can reliably decide that the sleeping person is in a state of imminently falling from a bed by deciding that the sleeping person is in a dangerous state when the region where the sleeping person exists is brought closer to one end of the bed than a predetermined distance.

Additionally, it is possible to know that the sleeping person is in a dangerous state at a location remote therefrom by providing informing means for, based on a signal output from signal outputting means, informing a third party that the sleeping person is in a dangerous state.

The informing means can urge a third party to swiftly deal with the situation by informing the third party that the sleeping person is in a dangerous state by voice, characters, symbols, intensity of light including interior illumination light, or vibrations through a telecommunication line.

The lighting pattern projecting means projects a lighting pattern that has a plurality of lighting spots, and the moving amount calculating means calculates an inter-frame moving amount of each lighting spot in an axial direction connecting the lighting pattern projecting means and the image pickup means while providing a positive or negative sign in accordance with a moving direction, and calculates an inter-frame moving amount of the lighting pattern by use of a moving amount of one or more of the lighting spots, whereby the moving amount of the lighting pattern can be easily calculated.

The lighting pattern projecting means projects a lighting pattern that has a plurality of lighting spots, and the moving amount calculating means calculates an inter-frame moving amount of each lighting spot in an axial direction connecting the lighting pattern projecting means and the image pickup means while providing a positive or negative sign in accordance with a moving direction, and calculates the total moving amount of each lighting spot as an inter-frame moving amount of the lighting pattern, whereby a statistical noise influence can be reduced.

The lighting pattern projecting means projects a lighting pattern that has a single slit ray or a plurality of slit rays, and the moving amount calculating means calculates an inter-frame moving amount of each lighting spot in an axial direction connecting the lighting pattern projecting means and the image pickup means while providing a positive or negative sign in accordance with a moving direction, and calculates an inter-frame moving amount of the lighting pattern by use of a moving amount of a pixel corresponding to the single or plural slit rays, whereby the moving amount of the lighting pattern can be easily calculated.

The lighting pattern projecting means projects a lighting pattern that has a single slit ray or a plurality of slit rays, and the moving amount calculating means calculates an inter-frame moving amount of each pixel corresponding to a slit ray in an axial direction connecting the lighting pattern projecting means and the image pickup means while providing a positive or negative sign in accordance with a moving direction, and calculates the total moving amount of each pixel corresponding to the slit ray as an inter-frame moving amount of the lighting pattern, whereby the number of measurement points can be increased, and a statistical noise influence can be reduced.

The lighting pattern projecting means is disposed directly above a part close to one end of an edge of bedding facing a head of or a foot of a person sleeping on the bedding, and the image pickup means is disposed directly above a part close to an opposite end thereof, whereby monitoring can be performed without allowing the sleeping person to have an intense consciousness of being monitored.

The provision of presence-in-bed detecting means for detecting the presence/absence of a sleeping person makes it possible to swiftly and accurately judge whether the sleeping person is absent or the sleeping person has stopped his/her breathing.

The provision of a pressure sensitive switch that can be placed under the sleeping person and can be used to detect the presence/absence of the sleeping person makes it possible to swiftly and accurately judge whether the sleeping person is absent or the sleeping person has stopped his/her breathing.

This specification includes the contents of the description and/or the drawings of Japanese Patent Application No. 2000-372820 on which the priority of this application is based.

BRIEF DESCRIPTION OF THE DRAWINGS

FIG. 2 is a schematic diagram explaining the calculation of an inter-frame moving amount of a lighting pattern on an image in a moving amount calculating means;

FIG. 8 is a schematic diagram showing a lighting pattern projected by the lighting pattern projecting means;

BEST MODE FOR CARRYING OUT THE INVENTION

The invention of this application has the aforementioned features, and embodiments thereof will hereinafter be described.

Figure 1:
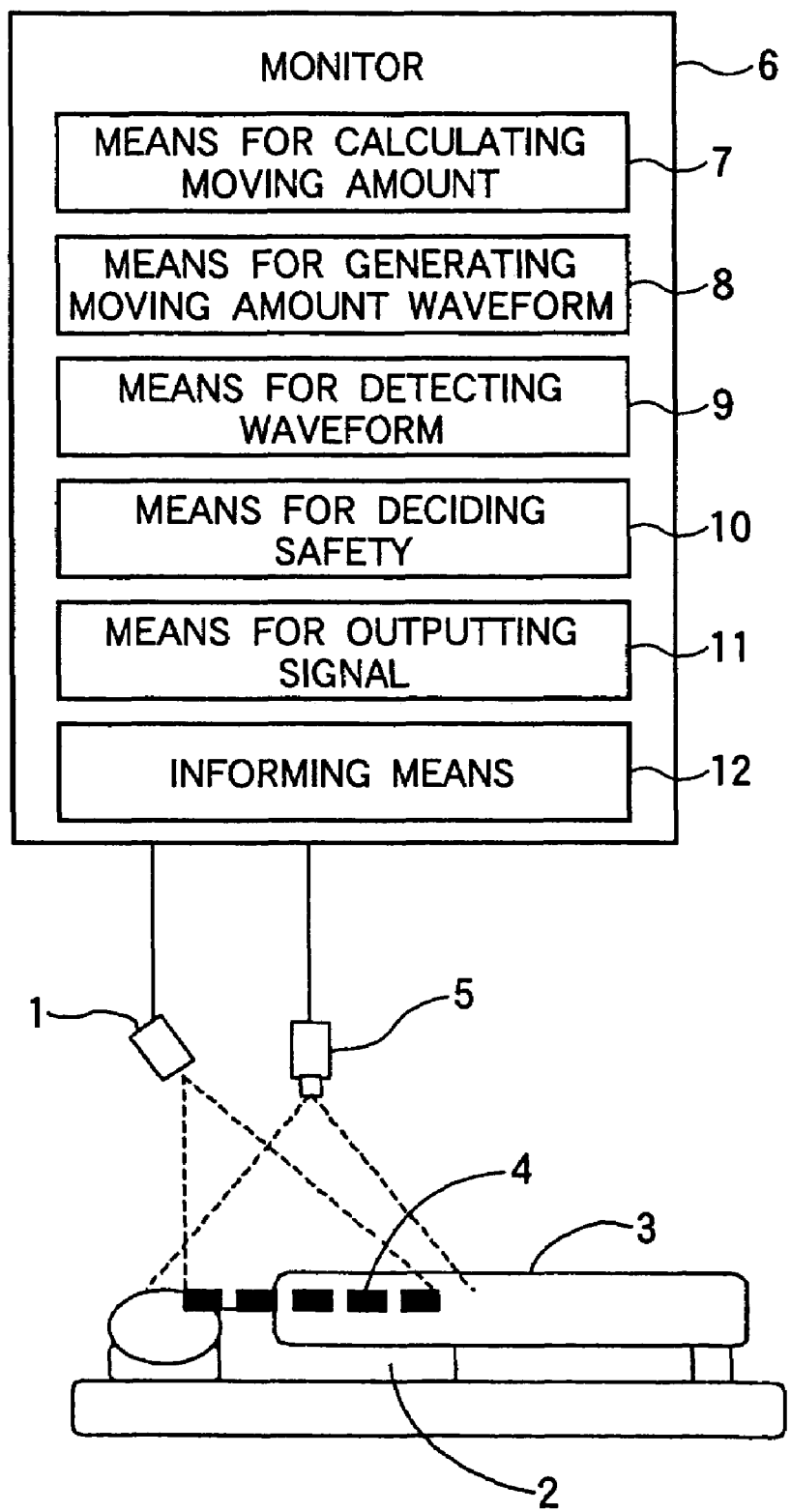
FIG. 1 is a schematic diagram showing the structure of a monitor according to the invention of this application.

FIG. 1 is a schematic diagram showing the structure of a monitor according to the invention of this application. The monitor 6 is composed of a lighting pattern projecting means 1, an image pickup means 5, a moving amount calculating means 7, a moving amount waveform generating means 8, a waveform detecting means 9, a safety deciding means 10, a signal outputting means 11, and an informing means 12. A lighting pattern 4 is first projected from the lighting pattern projecting means 1 onto a body 2 of a sleeping person or onto bedding 3. It is preferable to set the wavelength of projected light to be infrared rays, so as to project without allowing the sleeping person to have consciousness of being monitored. The lighting pattern 4 projected to the body 2 or the bedding 3 is continuously picked up as an image by the image pickup means 5. The image pickup means 5 can pick up, for example, an infrared ray that is a wavelength of the projected light. In response to a movement in an optical axial direction of the image pickup means resulting from a movement of the body 2 or resulting from a movement of the bedding 3 responding to the movement of the body 2, a movement of a lighting pattern, whose optical axis is different from that of the image pickup means, in an pickup image plane occurs, and an inter-frame moving amount of this lighting pattern is calculated by the moving amount calculating means 7 from two frames of images different in time that have been acquired by the image pickup means 5.

Thereafter, in the moving amount waveform generating means 8, moving amount waveform data is generated by arranging the inter-frame moving amounts calculated by the moving amount calculating means 7 in time series. Further, in the waveform detecting means 9, the body movement and respiratory movement of the sleeping person are detected from the moving amount waveform data. Even 2 or 3 frames/second of images to be acquired are enough to generate the waveform of respiration. Preferably, the images are acquired at regular intervals in order to generate the moving amount waveform data.

The monitor 6 of the invention of this application may be provided with the safety deciding means 10 by which the safety of a sleeping person is decided from the body movement and respiratory movement of the sleeping person detected by the waveform detecting means 9. When it is decided that the sleeping person is in a dangerous state in the safety deciding means 10, the signal outputting means 11 outputs a signal indicating it. As a result, the dangerous state can be recorded, for example, together with its time. Further, based on the signal output by the signal outputting means 11, the informing means 12 automatically informs a third party the sleeping person is in a dangerous state.

FIG. 2 is a schematic diagram explaining the calculation of an inter-frame moving amount of a lighting pattern on an image in the moving amount calculating means. In the moving amount calculating means 7, an inter-frame moving amount of the lighting pattern in an axial direction connecting the lighting pattern projecting means 1 and the image pickup means 5 is calculated from two frames different in time among images acquired by the image pickup means 5.

Figure 3:
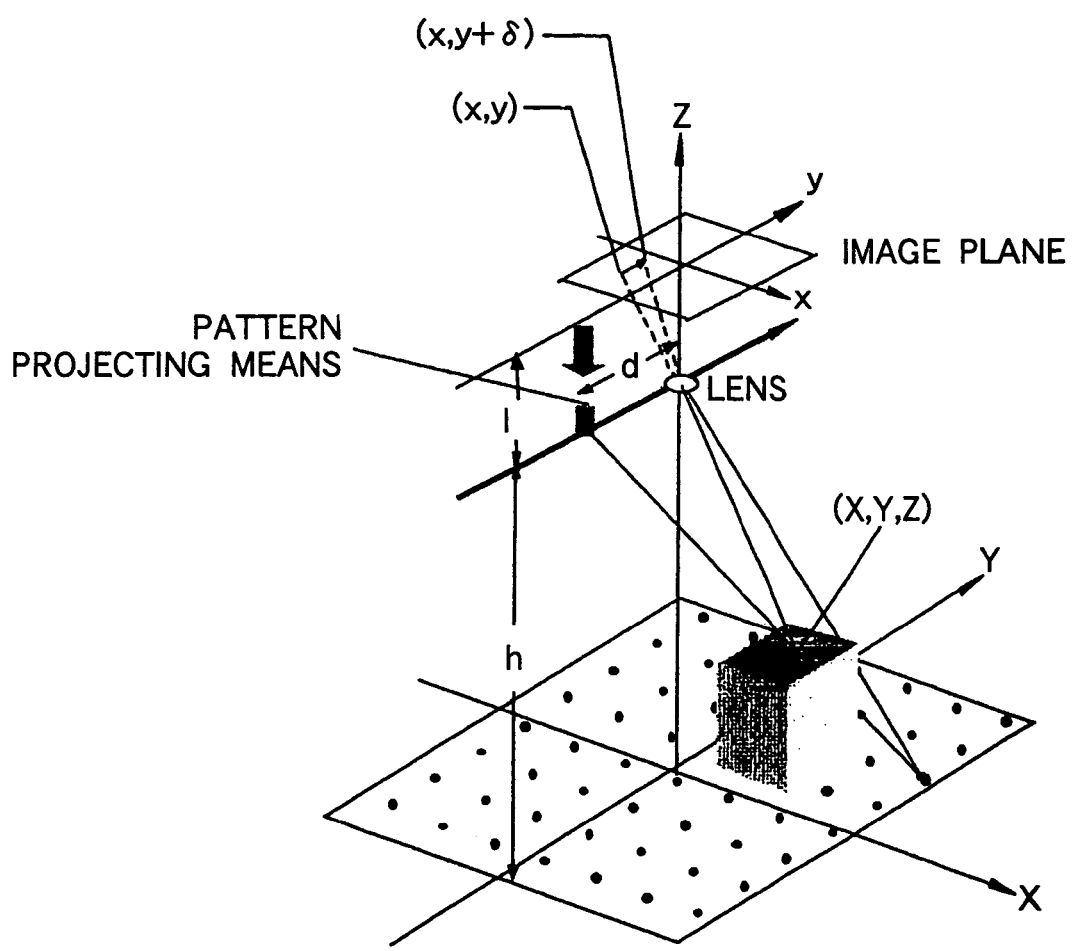
FIG. 3 is a schematic diagram showing the principle of the monitor according to the invention of this application.

FIG. 3 is a schematic diagram showing the principle of the monitor according to the invention of this application. In an optical arrangement shown in FIG. 3, the following equation is established.

$$\delta = dlZ/\{h(h-Z)\}$$

where
  δ: inter-frame moving amount of a lighting pattern,
  h: installation heights of the lighting pattern projecting means and the image pickup means,
  d: distance between the lighting pattern projecting means and the image pickup means,
  l: focal length of the image pickup means, and
  Z: displacement amount in the height direction.

That is, the inter-frame moving amount δ of the lighting pattern corresponds to a displacement amount Z in the height direction resulting from a movement of the body 2 of a sleeping person or resulting from a movement of bedding 3 in response to the movement of the body 2. Therefore, in the waveform detecting means 9, a waveform showing a periodic pattern can be detected as a respiratory pattern, and a waveform showing a variation having a high peak can be detected as a body movement pattern (i.e., pattern in which the waveform is varied by a body movement, such as turning over in bed) separately from each other in the moving amount waveform data generated by the moving amount waveform generating means 8. In the respiratory pattern, a respiration number per unit time can be known from its periodicity. Further, the time transition of the periodicity shows the stability of the respiration of the sleeping person. Further, since the inter-frame moving amount of the lighting pattern corresponds to a displacement amount in the height direction as mentioned above, it serves also as a means for knowing the depth of the respiration.

A predominant frequency component can be calculated by conducting a frequency analysis of moving amount waveform data or respiratory pattern with discrete Fourier transform or discrete wavelet transform, and a respiration number per unit time can also be calculated from the value of this frequency. Fast Fourier transform can be mentioned as a typical example of discrete Fourier transform. For example, on the assumption that the most prominent sample in a result obtained by applying fast Fourier transform to the respiratory pattern is the M-th sample in sampling data in which N samples of respiratory patterns have been sampled at sampling intervals of Δt second, the most prominent frequency f can be obtained by M/(Δt×N), and a respiration number per minute can be obtained by 60×f. A respiration period can be obtained by 1÷f. As a matter of course, various frequency analysis techniques other than fast Fourier transform can be applied in the invention of this application.

In the safety deciding means 10, for example,
  (i) when the period of a respiratory pattern falls into disarray in a short time,
  (ii) when the period of a respiratory pattern suddenly changes,
  (iii) when a respiratory pattern continuously disappears, and
  (iv) when a body movement pattern frequently appears in a short time, it is decided that a sleeping person is in a dangerous state. The condition of (i) or (ii) is considered to be caused by an infirmity of the lungs, such as spontaneous pneumothorax or bronchial asthma, a cardiopathy, such as congestive heart failure, or a cerebrovascular disease, such as cerebral hemorrhage. The condition of (iii) appears when respiration stops. A possible condition of (iv) is the fact that the sleeping person suffers from some reason and is in distress.

Figure 4:
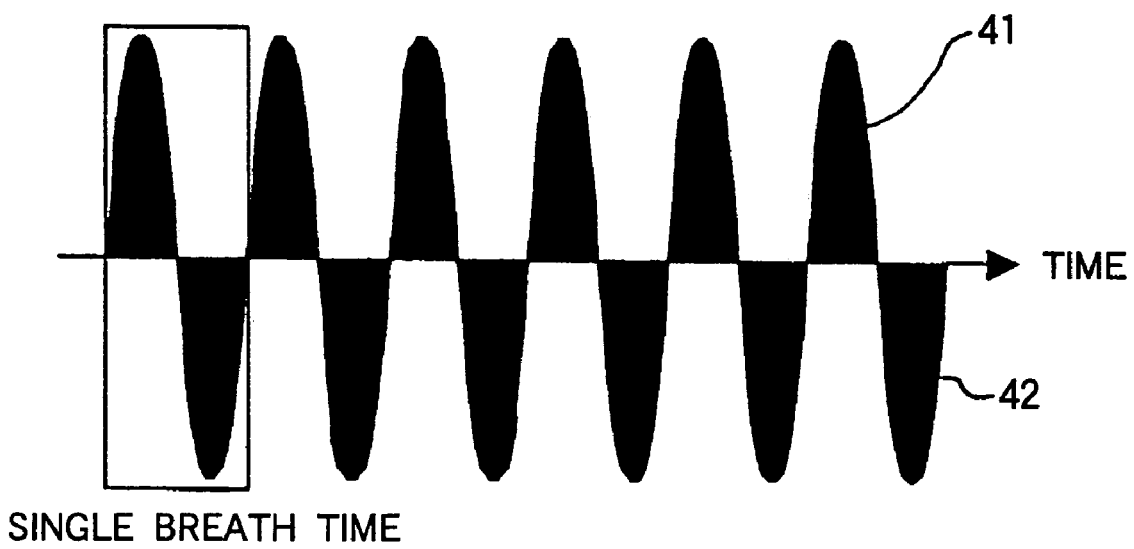
FIG. 4 shows an example of a waveform pattern of moving-amount waveform data.

In the moving amount calculating means 7, preferably, an inter-frame moving amount of a lighting pattern in an axial direction connecting the lighting pattern projecting means 1 and the image pickup means 5 is calculated from two frames of images different in time while applying a positive or negative sign in accordance with a moving direction. Hereby, concerning the respiration, an expiratory pattern and an inspiratory pattern shown in FIG. 4 are always obtained, and the respiration can be counted by measuring the number of "zero crosses" (intersections where the sign is reversed) appearing from the expiratory pattern to the inspiratory pattern or from the inspiratory pattern to the expiratory pattern. This is advantageous when processing is performed by a computer.

FIG. 4 shows an example of a waveform pattern of moving-amount waveform data. The moving amount waveform data generated by the moving amount waveform generating means 8 shows a waveform pattern, for example, shown in FIG. 4.

Figure 5:
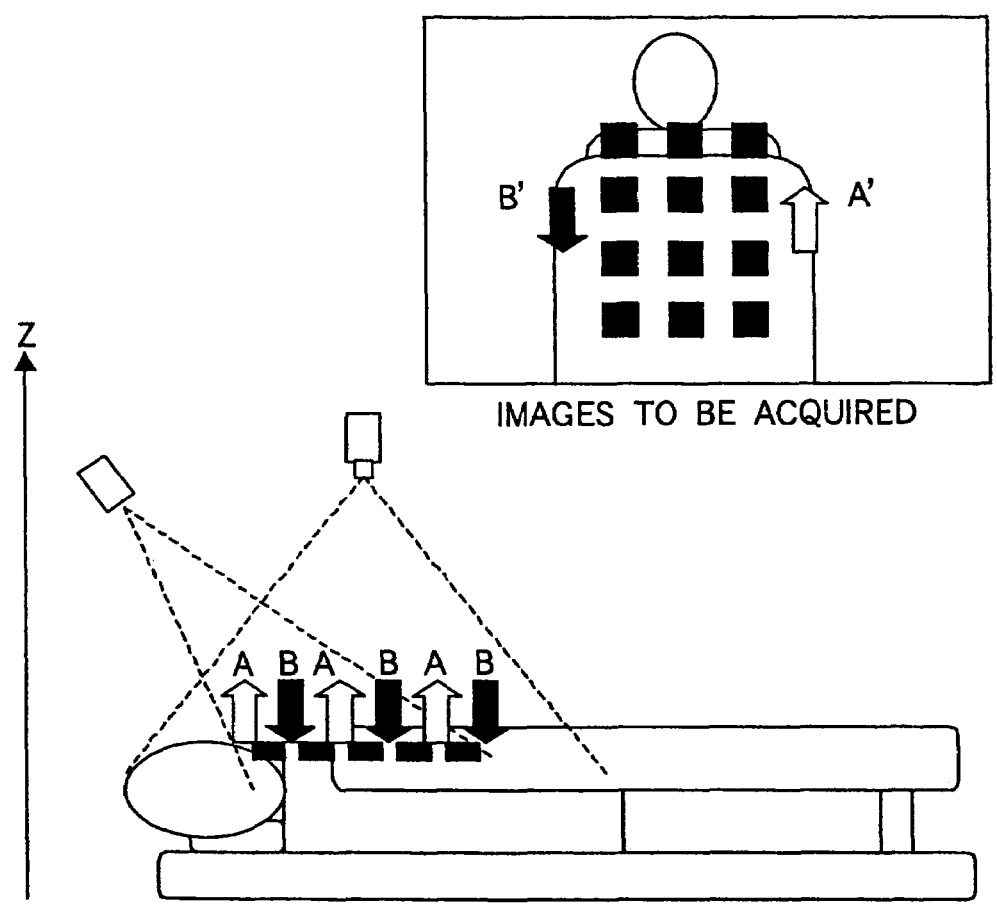
FIG. 5 is a schematic diagram showing the principle of the respiratory movement detection of the monitor according to the invention of this application.
Figure 6A:
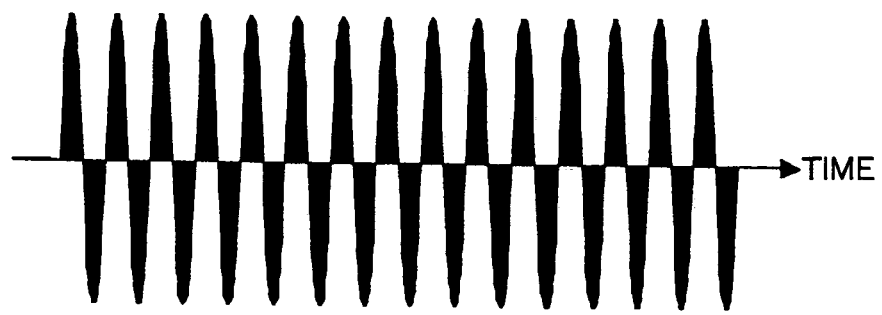
FIG. 6(*a*), FIG. 6(*b*), FIG. 6(*c*), and FIG. 6(*d*) show examples of normal and abnormal respiratory patterns.
Figure 6B:
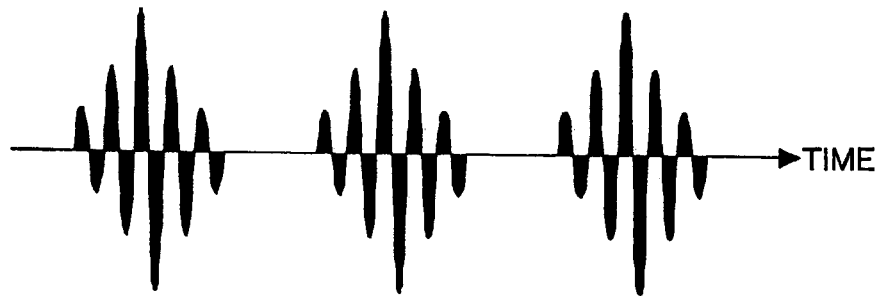
Figure 6C:
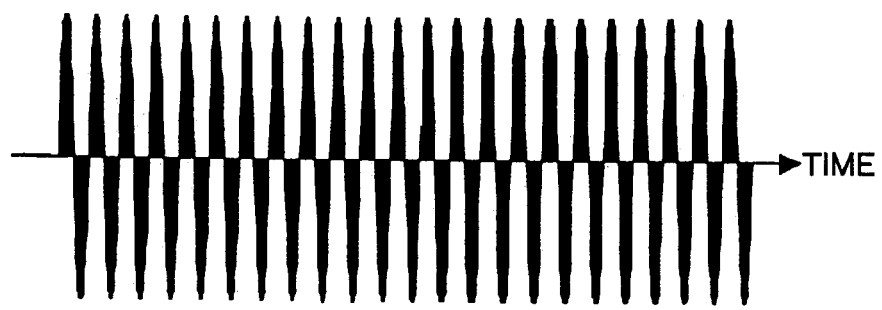
Figure 6D:
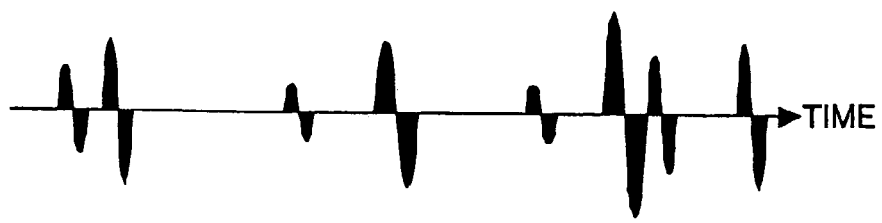

FIG. 5 is a schematic diagram showing the principle of the respiratory movement detection of the monitor according to the invention of this application. In an optical arrangement shown in FIG. 5, when the height changes upward "A," a lighting pattern on an image moves in a direction "A'" from the image pickup means to the lighting pattern projecting means. In contrast, when the height changes downward "B," the lighting pattern on the image moves in a direction "B'" from the lighting pattern projecting means to the image pickup means on the image.

Therefore, concerning the inter-frame moving amount of the lighting pattern, if moving a mount waveform data is generated from the inter-frame moving amount calculated while having a positive or negative sign in accordance with the moving direction, and if a waveform showing a periodic pattern among the moving amount waveform data is detected as a respiratory pattern, a part 41 having a sign corresponding to a movement in the direction "A'" can be detected as an expiratory pattern, whereas a part 42 having a sign corresponding to a movement in the direction "B'" can be detected as an inspiratory pattern among the detected respiratory patterns.

Since the moving direction of a lighting pattern follows a horizontal or vertical direction in the picked-up image by setting the horizontal or vertical direction of a picked-up image to coincide with the axial direction connecting the lighting pattern projecting means and the image pickup means, the moving amount of the lighting pattern can be easily calculated.

Further, a respiration number per unit time (or respiration period) can be known by a time point where the part 41 having a sign corresponding to a movement in the direction "A'" and the part 42 having a sign corresponding to a movement in the direction "B'" each appear once as a single breath.

In the safety deciding means, a decision may be made as to whether the respiration of a sleeping person is a normal respiration by pre-storing each respiratory pattern concerning normal and abnormal respirations and comparing these with a respiratory pattern of the sleeping person.

FIG. 6(*a*), FIG. 6(*b*), FIG. 6(*c*), and FIG. 6(*d*) show examples of normal and abnormal respiratory patterns. A normal respiratory pattern to be registered is a periodic pattern shown in FIG. 6(*a*). On the other hand, a respiratory pattern, such as Cheyne-Stokes respiration, central hyperventilation, ataxic respiration, or Kussmaul respiration, that is considered to occur when a physiologically disorder arises in the body, is registered as an abnormal respiratory pattern. As an example, a respiratory pattern of Cheyne-Stokes respiration is shown in FIG. 6(*b*), a respiratory pattern of central hyperventilation is shown in FIG. 6(*c*), and a respiratory pattern of ataxic respiration is shown in FIG. 6(*d*). These respiratory patterns are obviously different in the waveform from the normal respiratory pattern, and a decision is made as to a respiratory pattern to which that of a sleeping person belongs on the basis of the fact that they are different in the frequency of respiration, the occurrence count thereof, and the depth thereof.

When it is decided that the respiration of the sleeping person belongs to a respiratory pattern that is considered to occur when physiologically disorders arise in the body, the safety deciding means decides that the sleeping person is carrying out abnormal respiration and is in a dangerous state. When the sleeping person displays abnormal respiration, the informing means may inform a third party about the name of the respiratory pattern of the sleeping person, the name of a disease considered to cause the respiration, the disease organ, the disease part, etc. Table 1 shows the disease name or disease part when the abnormal respiratory pattern occurs.

TABLE 1

| | |
|---|---|
| Cheyne-Stokes respiration | Disorder under both-sides cerebral cortex and of diencephalon |
| Central hyperventilation | Disorder from lower midbrain to upper pons |
| Ataxic respiration | Disorder from lower pons to upper medulla oblongata |
| Kussmaul respiration | Diabetic coma or uremia |

Figure 7:
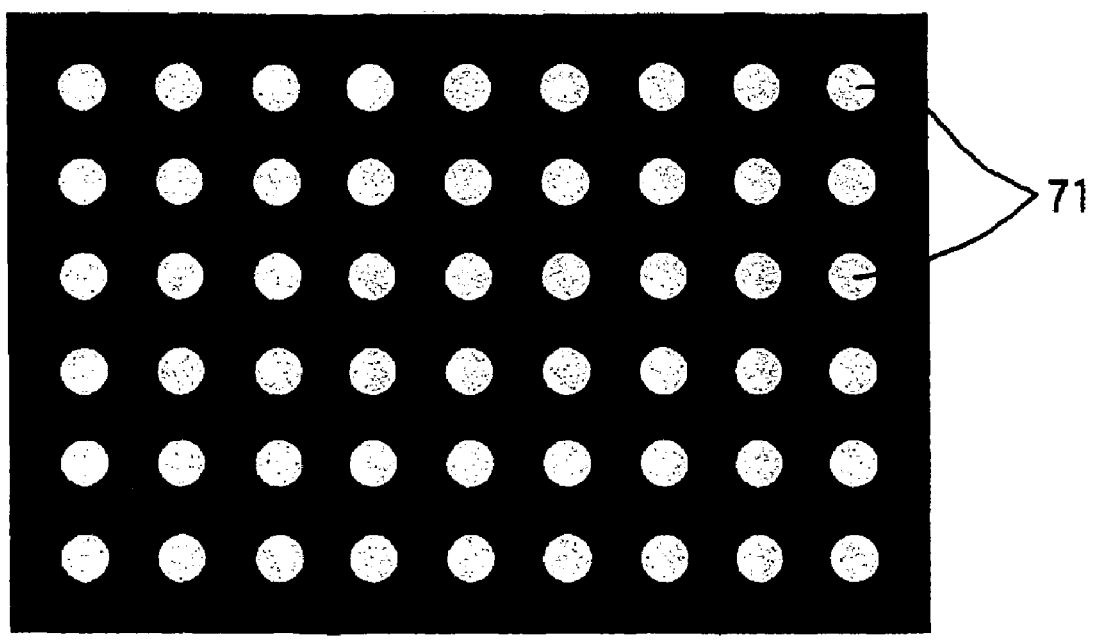
FIG. 7 is a schematic diagram showing a lighting pattern projected by a lighting pattern projecting means.

FIG. 7 and FIG. 8 are each a schematic diagram showing a lighting pattern projected by the lighting pattern projecting means. Preferably, a lighting pattern projected by the lighting pattern projecting means has a spatially discrete distribution. For example, a plurality of lighting spots 71 shown in FIG. 7, a single slit ray 81 shown in FIG. 8, or a plurality of slit rays 82 are selected and used.

In a lighting pattern having a plurality of lighting spots, an inter-frame moving amount of each lighting spot is calculated while adding a positive or negative sign in accordance with a moving direction, and the total moving amount of each lighting spot is calculated as an inter-frame moving amount of the lighting pattern. Likewise, in a lighting pattern having a single or a plurality of slit rays, an inter-frame moving amount of each pixel corresponding to the slit ray is calculated while adding a positive or negative sign in accordance with a moving direction, and the total moving amount of each pixel corresponding to the slit ray is calculated as an inter-frame moving amount of the lighting pattern. A statistical noise influence can be reduced by calculating the total inter-frame moving amount when spatially discrete lighting patterns are used.

In the moving amount calculating means, a region in an image where the inter-frame moving amount of a lighting pattern appears greatly or where an inter-frame movement of the lighting pattern appears frequently is determined as a region where the sleeping person exists. When this region frequently moves in a short time, the safety deciding means may decide that the sleeping person is in a dangerous state. This can be regarded as a condition where the sleeping person suffers from some reason and is in distress.

The safety deciding means may decide that the sleeping person is in a dangerous state when the region where the sleeping person exists is brought extremely close to one of the sides of a bed and when the sleeping person on the bed is being monitored. This can be regarded as a situation where the sleeping person is in a dangerous position as if to fall from the bed.

In the monitor of the invention of this application, preferably, a range where the lighting pattern is projected is set within a range covering positions that can be occupied by the belly, chest, back, and shoulders of the sleeping person. Likewise, preferably, a range of a region photographed by an image pickup device is set within a range covering positions that can be occupied by the belly, chest, back, and shoulders of the sleeping person.

Figure 9:
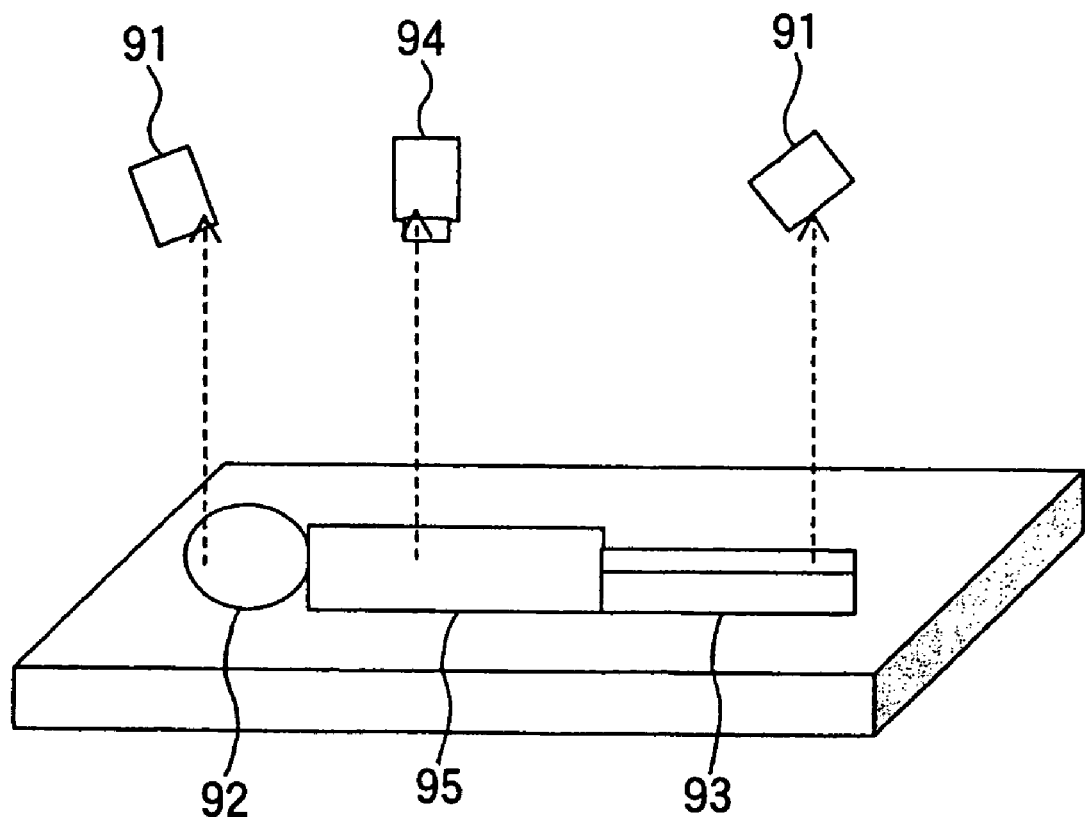
FIG. 9 is a schematic diagram showing an arrangement of the lighting pattern projecting means and an image pickup means.
Figure 10:
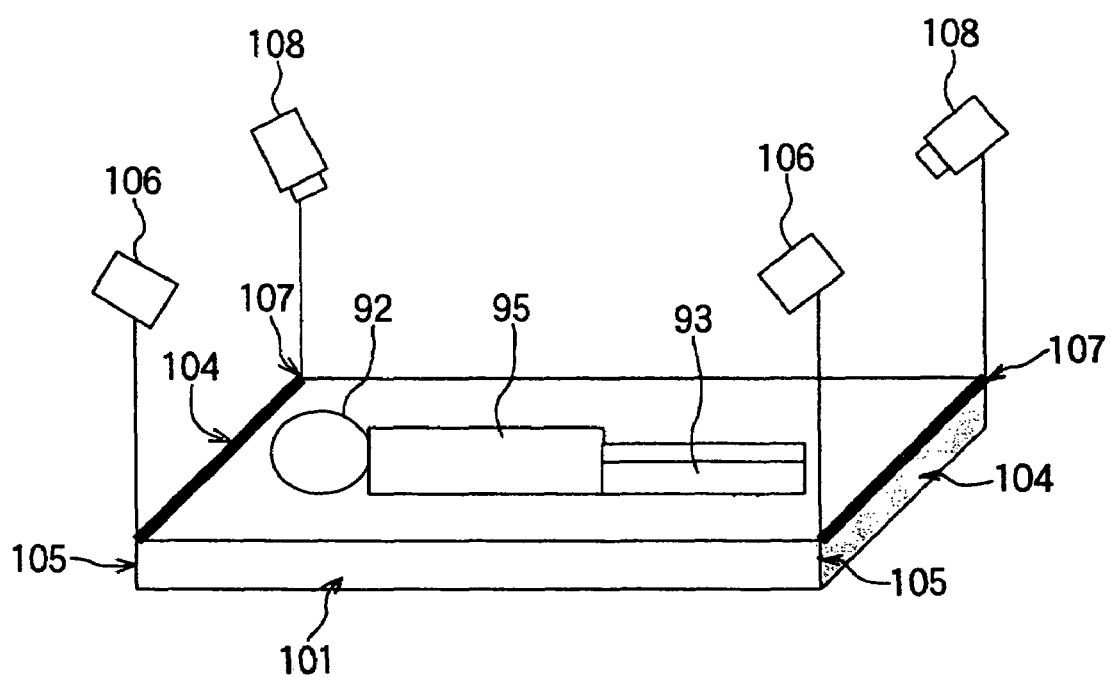
FIG. 10 is a schematic diagram showing an arrangement of the lighting pattern projecting means and the image pickup means.
Figure 11:
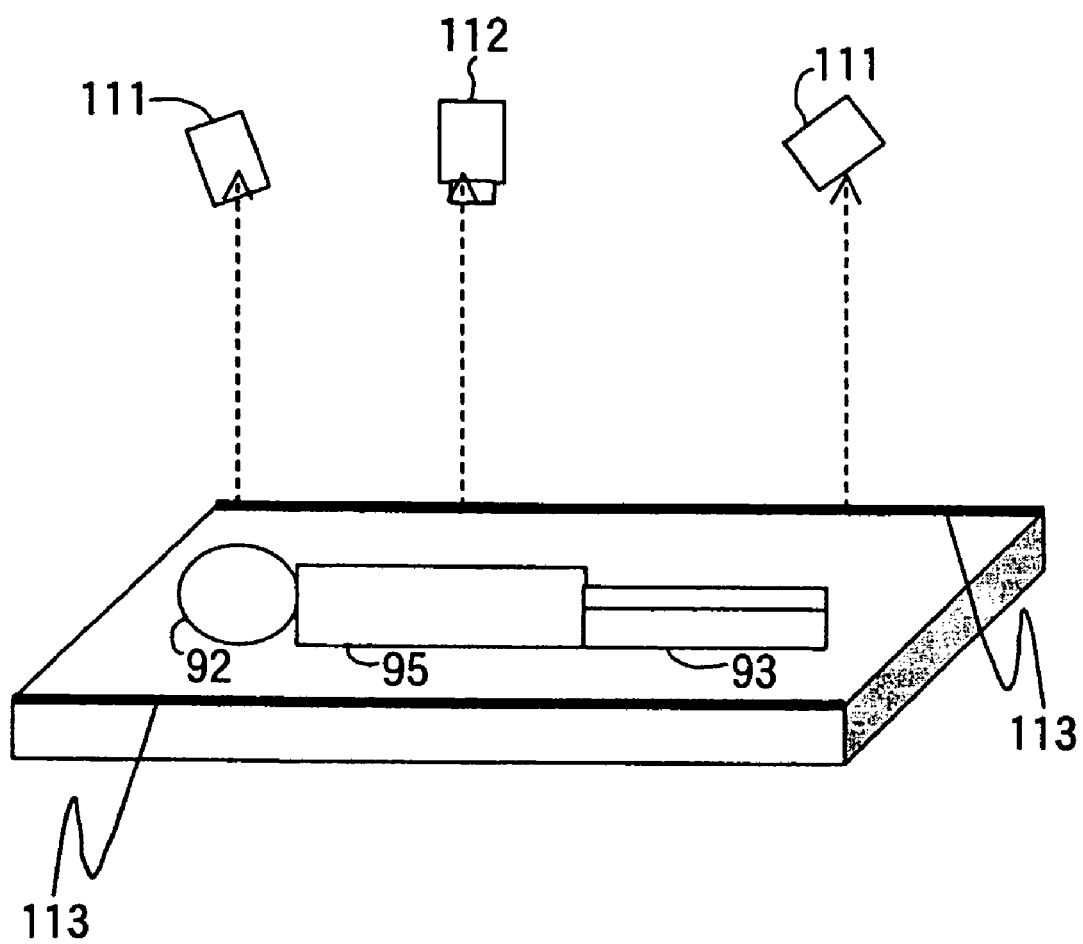
FIG. 11 is a schematic diagram showing an arrangement of the lighting pattern projecting means and the image pickup means.

FIG. 9 and FIG. 10 are each a schematic diagram showing an arrangement of the lighting pattern projecting means and the image pickup means. For example, as shown in FIG. 9, the lighting pattern projecting means 91 is disposed directly above a part close to the head 92 or the foot 93 of the sleeping person, and the image pickup means 94 is disposed directly above a part around the belly 95 of the sleeping person. At an edge 104 of bedding 101 placed under the sleeping person facing the head 92 or the foot 93 of the sleeping person as shown in FIG. 10, the lighting pattern projecting means 106 may be disposed directly above a part close to one end 105 of the edge 104, and the image pickup means 108 may be disposed directly above a part close to an opposite end 107 of the edge 104. The arrangement shown in FIG. 9 can capture the respiratory movement of the sleeping person extremely sensitively, and has the advantage of being able to detect a detailed respiratory pattern. However, since the image pickup device comes into view of the sleeping person, there can be a case in which the arrangement is accompanied by a psychologically oppressive feeling. In contrast, an arrangement shown in FIG. 10 cannot specifically catch the respiration unlike the arrangement shown in FIG. 9, but this arrangement is considered to have a weaker psychologically oppressive feeling. Of course, the arrangement shown in FIG. 9 can be formed to sacrifice slightly the sensitivity of respiratory movement as in FIG. 11, and an oppressive feeling may be reduced by disposing the lighting pattern projecting means 111 and the image pickup means 112 at one side end 113 of the bedding. These arrangements are to be appropriately selected depending on the situation.

Any type of lighting pattern projecting means can be used if the lighting pattern projecting means can project light spatially discretely. Use can be made of, for example, a fiber grating, a diffraction grating, a lens array, a formed image of a light source array or an aperture array, a device that collimates an outgoing beam of the light source array or the aperture array, etc.

In the monitor of the invention of this application, as an auxiliary means for accurately detecting whether a sleeping person is present or absent, a pressure sensitive switch may be disposed in the bedding placed under the sleeping person. The presence/absence of the sleeping person is determined by ON/OFF of this switch.

Further, in the monitor of the invention of this application, the informing means has a voice outputting function and informs a third party by voice that the sleeping person is in a dangerous state. It may inform the third party by characters, symbols, intensity of light including interior illumination light, or vibrations. Further, the informing means may have a function to connect to a telecommunications line, such as a general telephone line, ISDN line, PHS line, or cellular telephone line, and may inform the third party by voices, characters, or symbols that the sleeping person is in a dangerous state.

Figure 12:
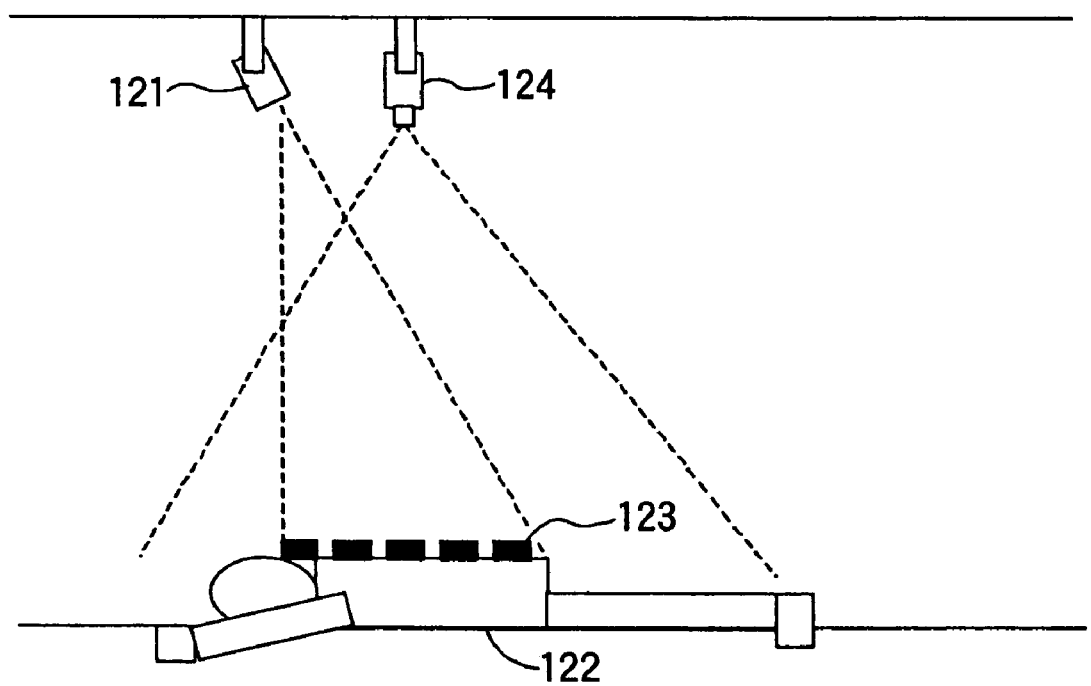
FIG. 12 is a schematic diagram showing the structure of an indoor safety monitor that is the invention of this application.

FIG. 12 is a schematic diagram showing an arrangement of the lighting pattern projecting means and the image pickup means. The principle of the invention of this application is not applied limitedly to a monitor for a sleeping person, of course. For example, as a matter of course, the principle can be applied also to an indoor safety monitor that monitors the safety of a person in a room. The indoor safety monitor has the same structure as the monitor of the invention of this application, and is shown, for example, in FIG. 12.

First, a lighting pattern 123 is projected from a lighting pattern projecting means 121 to a body 122 of a person to be monitored. The lighting pattern 123 projected to the body 122 is continuously picked up as an image by an image pickup means 124, and, from two frames of images different in time acquired by the image pickup means 124, an inter-frame moving amount of the lighting pattern 123 resulting from a movement of the body 122 is calculated by the moving amount calculating means.

Thereafter, in the moving amount waveform generating means, moving amount waveform data is generated by arranging the inter-frame moving amounts calculated by the moving amount calculating means in time series. Further, in the waveform detecting means, a body movement and respiratory movement of the person to be monitored are detected from the moving amount waveform data.

The indoor safety monitor is provided with a safety deciding means. From the body movement and respiratory movement of the person detected by the waveform detecting means, the safety deciding means decides whether the person to be monitored is safe or not. When the safety deciding means decides that the person is in a dangerous state, the informing means automatically informs a third party the person to be monitored is in a dangerous state.

In the moving amount calculating means, an inter-frame moving amount of a lighting pattern on an image in an axial direction connecting the lighting pattern projecting means 121 and the image pickup means 124 is calculated from two frames different in time among images acquired by the image pickup means 124.

In the waveform detecting means, a waveform indicating a periodic pattern is detected as a respiratory pattern, whereas a waveform indicating a variation having a high peak is detected as a body movement pattern among the moving amount waveform data generated by the moving amount waveform generating means.

The safety deciding means decides that a time zone where a body-movement pattern of the person to be monitored disappears indicates a state where the person stops moving, and, in this time zone, the safety deciding means decides that the person is in a dangerous state when the period of the respiratory pattern falls into disarray in a short time, when the period of the respiratory pattern suddenly changes, or when the respiratory pattern continuously disappears.

Figure 13:
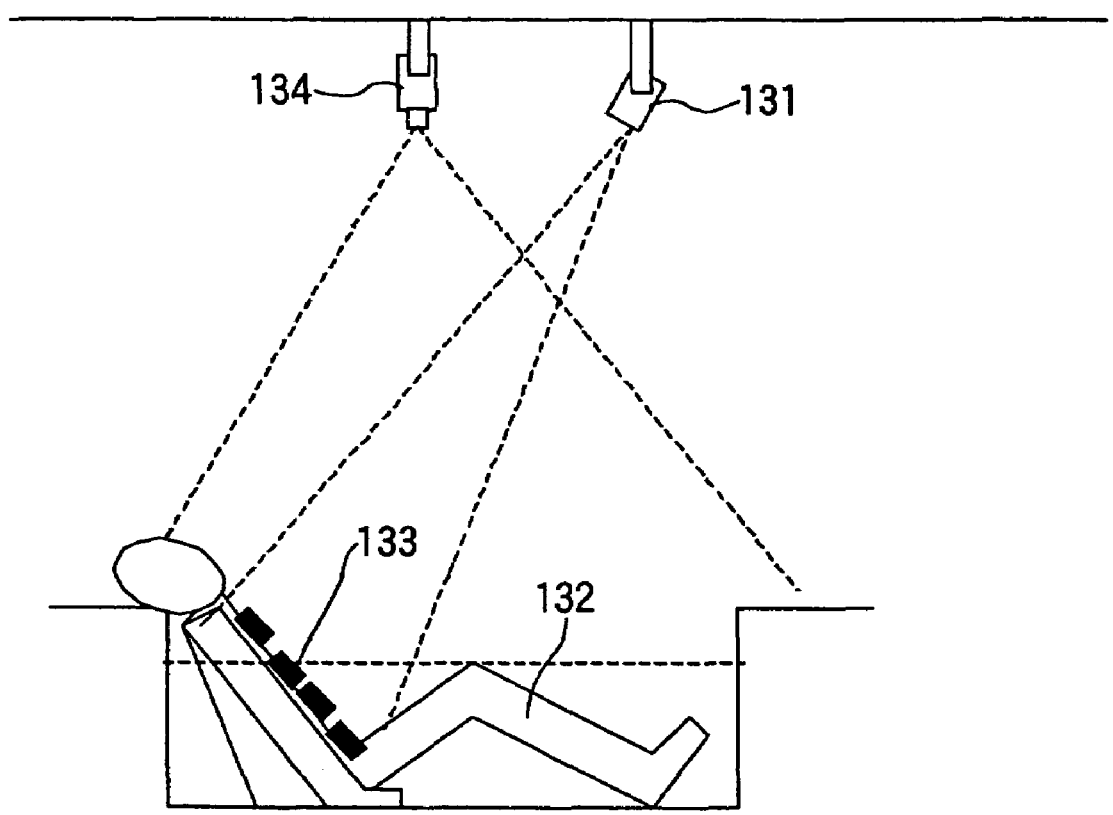
FIG. 13 is a schematic diagram showing the structure of an indoor safety monitor that is the invention of this application.

The indoor safety monitor mentioned above works effectively especially when a monitoring region is limited. For example, this is extremely adaptable for monitoring a person having a bath as shown in FIG. 13. Likewise, this works effectively to monitor the safety of a person in a bathroom.

The present invention is not limited to the aforementioned embodiments.

It is permissible to project light that has been subjected to amplitude modulation and extract a modulating signal from a picked-up signal. Thereby, it is possible to reduce an influence by which general light, such as indoor illumination light, is changed into a noise.

If precision is sacrificed to some degree, the frame may be a field. Therefore, the frame set forth in the appended claims has a broad concept including a field.

INDUSTRIAL APPLICABILITY

As described in detail in the foregoing description, according to the invention of this application, it is possible to provide a monitor by image measurement capable of reliably detecting the respiratory movement of a sleeping person and easily making a quantitative evaluation of the detected respiratory movement without being influenced by the posture of the sleeping person, illumination light, and design of a quilt.

The invention of this application is strongly expected to be put into practical use as a technique that can support the achievement of swift emergency treatment when a senior citizen or sick person falls into a crisis condition.

All publications, patents, and patent applications cited in the present specification are to be employed in the present specification as references without any changes.

What is claimed is:

1. A monitor comprising:
   lighting pattern projecting means for projecting a specified lighting pattern;
   image pickup means, whose optical axis is different from that of the lighting pattern projecting means, for picking up light of a projected wavelength continuously;
   moving amount calculating means for calculating an inter-frame moving amount of the lighting pattern from two frames of images acquired by the image pickup means at different times;
   moving amount waveform generating means for generating moving amount waveform data comprising inter-frame moving amounts arranged in time series; and
   waveform detecting means for detecting a movement of an object to be picked up from the moving amount waveform data;
   wherein the lighting pattern projecting means projects the lighting pattern that has a plurality of lighting spots or slit rays; and
   the moving amount calculating means calculates an inter-frame moving amount of each lighting spot in an axial direction connecting the lighting pattern projecting means and the image pickup means while providing a positive or negative sign in accordance with a moving direction, and calculates a sum of moving amounts of pixels corresponding to the plurality of lighting spots or slit rays.

2. The monitor as set forth in claim 1, wherein the waveform detecting means detects a body movement and respiratory movement of a sleeping person, the monitor further comprising:
   safety deciding means for deciding the safety of the sleeping person from the body movement and respiratory movement of the sleeping person; and
   signal outputting means for, when the safety deciding means decides that the sleeping person is in a dangerous state, outputting a signal indicating it.

3. The monitor as set forth in claim 2, wherein the moving amount calculating means calculates an inter-frame moving amount in a partial region of the lighting pattern in an axial direction connecting the lighting pattern projecting means and the image pickup means, and determines a region in an image where an inter-frame moving amount in the partial region appears much greater than a predetermined amount or where an inter-frame movement in the partial region appears frequently beyond a predetermined amount as a region where the sleeping person exists, and the safety deciding means decides that the sleeping person is in a dangerous state when the region where the sleeping person exists moves in a shorter time than a predetermined time and moves frequently beyond a predetermined amount.

4. The monitor as set forth in claim 2, wherein the moving amount calculating means calculates an inter-frame moving amount in a partial region of the lighting pattern in an axial direction connecting the lighting pattern projecting means and the image pickup means, and determines a region in an image where an inter-frame moving amount in the partial region appears much greater than a predetermined amount or where an inter-frame movement in the partial region appears more frequently than a predetermined frequency as a region where the sleeping person exists, and the safety deciding means decides that the sleeping person is in a dangerous state when the region where the sleeping person exists is brought closer to one end of the bed than a predetermined distance.

5. The monitor as set forth in claim 2, comprising informing means for, based on a signal output from signal outputting means, informing a third party that the sleeping person is in a dangerous state.

6. The monitor as set forth in claim 5, wherein the informing means informs the third party that the sleeping person is in a dangerous state by voices, characters, symbols, intensity of light including interior illumination light, or vibrations through a telecommunications line.

7. The monitor as set forth in claim 2, wherein the waveform detecting means detects a periodic pattern as a respiratory pattern, and detects a variation having a high peak as a body movement pattern from the moving amount waveform data.

8. The monitor as set forth in claim 7, wherein the safety deciding means decides that the sleeping person is in a dangerous state when a period of the respiratory pattern falls into disarray in a short time, when the period of the respiratory pattern suddenly changes, when the respiratory pattern continuously disappears, or when the body movement pattern frequently appears in a short time.

9. The monitor as set forth in claim 7, wherein from among respiratory patterns, the waveform detecting means detects a value having a positive or negative sign corresponding to a movement in a direction from the lighting pattern projecting means to the image pickup means on an image and a value having a positive or negative sign corresponding to a movement in a direction from the image pickup means to the lighting pattern projecting means on the image as an expiratory pattern and as an inspiratory pattern, respectively, or vice versa.

10. The monitor as set forth in claim 9, wherein the safety deciding means decides whether respiration belongs to normal respiration, Cheyne-Stokes respiration, central hyperventilation, ataxic respiration, or Kussmaul respiration from expiratory patterns and inspiratory patterns and decides that the sleeping person is in a dangerous state when the respiration belongs to any one of Cheyne-Stokes respiration, central hyperventilation, ataxic respiration, and Kussmaul respiration.

11. The monitor as set forth in claim 1, wherein the waveform detecting means detects a periodic pattern as a respiratory pattern, and detects a variation having a high peak as a body movement pattern form the moving amount waveform data.

12. The monitor as set forth in claim 11, wherein the safety deciding means decides that the sleeping person is in a dangerous state when a period of the respiratory pattern falls into disarray in a short time, when the period of the respiratory pattern suddenly changes, when the respiratory pattern continuously disappears, or when the body movement pattern frequently appears in a short time.

13. The monitor as set forth in claim 11, wherein from among respiratory patterns, the waveform detecting means detects a value having a positive or negative sign corresponding to a movement in a direction from the lighting pattern projecting means to the image pickup means on an image and a value having a positive or negative sign corresponding to a movement in a direction from the image pickup means to the lighting pattern projecting means on the image as an expiratory pattern and as an inspiratory pattern, respectively, or vice versa.

14. The monitor as set forth in claim 13, wherein the waveform detecting means counts zero crosses where signs are reversed between an expiratory pattern and an inspiratory pattern and counts respirations.

15. The monitor as set forth in claim 14, wherein the waveform detecting means calculates a respiration number per unit time or a respiration period from the counted respirations.

16. The monitor as set forth in claim 13, wherein the waveform detecting means calculates a respiration number per unit time or a respiration period by conducting a frequency analysis of the moving-amount waveform data or the sampling data obtained by sampling respiratory patterns, by calculating the most prominent frequency from a resulting frequency spectrum, and by calculating the respiration number per unit time or the respiration period from this frequency.

17. The monitor as set forth in claim 1, wherein the waveform detecting means calculates a respiration number per unit time or a respiration period by conducting a frequency analysis of the moving-amount waveform data or the sampling data obtained by sampling respiratory patterns, by calculating the most prominent frequency from a resulting frequency spectrum, and by calculating the respiration number per unit time or the respiration period from this frequency.

18. The monitor as set forth in claim 17, wherein the waveform detecting means conducts a frequency analysis with discrete Fourier transform or discrete wavelet transform.

19. The monitor as set forth in claim 1, wherein the lighting pattern projecting means is disposed directly above a part close to one end of an edge of bedding facing a head or a foot of a person sleeping on the bedding, and the image pickup means is disposed directly above a part close to an opposite end thereof.

20. The monitor as set forth claim 1, comprising presence-in-bed detecting means for detecting the presence/absence of a sleeping person.

21. The monitor as set forth in claim 1, comprising a pressure sensitive switch that can be placed under the sleeping person and can be used to detect the presence/absence of the sleeping person.

22. The monitor as set forth in claim 1, wherein the moving amount calculating means calculates an inter-frame moving amount of a lighting pattern in an axial direction connecting the lighting pattern projecting means and the image pickup means.

* * * * *